United States Patent [19]

Charbonneau et al.

[11] Patent Number: 4,925,517

[45] Date of Patent: May 15, 1990

[54] METHOD OF FORMING FRAGRANCE RELEASING PULL-APART SHEETS

[75] Inventors: Jack W. Charbonneau, Somerset, Wis.; Jerold O. Bahls, St. Paul, Minn.

[73] Assignee: Minnesota Mining and Manufacturing Company, St. Paul, Minn.

[21] Appl. No.: 378,433

[22] Filed: Jul. 10, 1989

Related U.S. Application Data

[63] Continuation of Ser. No. 211,870, Jun. 27, 1988, abandoned.

[51] Int. Cl.$^5$ .......................... B32B 31/12; B32B 5/16
[52] U.S. Cl. .................................... 156/276; 156/254; 156/308.6; 428/402.2; 428/905
[58] Field of Search ............... 156/310, 314, 254, 276, 156/344, 308.6, 305; 428/402.2, 905; 427/153, 214

[56] References Cited

U.S. PATENT DOCUMENTS

| | | | |
|---|---|---|---|
| 3,904,803 | 9/1975 | Brown et al. | 428/320 |
| 4,186,743 | 2/1980 | Steiger | 128/284 |
| 4,487,801 | 12/1984 | Turnbull et al. | 428/313.5 |
| 4,606,956 | 8/1986 | Charbonneau et al. | 428/40 |
| 4,661,388 | 4/1987 | Charbonneau | 428/43 |
| 4,720,417 | 1/1988 | Sweeny et al. | 428/201 |

*Primary Examiner*—Michael W. Ball
*Assistant Examiner*—Michele K. Yoder
*Attorney, Agent, or Firm*—Donald M. Sell; Walter N. Kirn; Mark A. Litman

[57] ABSTRACT

Fragrance releasing pull-apart sheets may be more consistently and easily manufactured by coating opposed surfaces with a binder, placing microcapsules between the two surfaces with binder, and adhering the surfaces together with the binder and/or additional binder applied with the capsules.

4 Claims, No Drawings

METHOD OF FORMING FRAGRANCE RELEASING PULL-APART SHEETS

This is a continuation of application Ser. No. 07/211,870 filed June 27, 1988, now abandoned.

FIELD OF THE INVENTION

This invention relates to microencapsulated materials, articles containing microencapsulated materials and the method of preparing such articles In particular, the present invention relates to microencapsulated materials adhesively secured between two temporarily adhered coated paper surfaces such that upon separation of said two surfaces, the capsules rupture, releasing material contained therein.

BACKGROUND OF THE INVENTION

Encapsulated materials have been used for many years in a wide variety of commercial applications. Early uses of encapsulated materials included paper coated with capsules bearing coloring material therein which could be used as a recording medium. U.S. Pat. No. 3,016,308 discloses one of the early efforts using encapsulated material as the image source on recording paper. U.S. Pat. Nos. 4,058,434 and 4,201,404 show other methods of application of encapsulated coloring materials on paper substrates to be used as imaging media and the like. U.S. Pat. No. 3,503,783 shows microcapsules having coloring material therein which are rupturable by the application of heat, pressure and/or radiation because of a metal coating on the surface of the capsule. These rupturable microcapsules, in one embodiment, may be secured between a substrate and a photoconductive top coat to enable photosensitive imaging of the system.

A wide variety of processes exist by which microcapsules can be manufactured. These varied processes provide different techniques for producing capsules of varying sizes, alternative materials for the composition of the capsule shell and various different functional materials within the shell. Some of these various processes are shown in U.S. Pat. Nos. 3,516,846; 3,516,941; 3,778,383; 4,087,376; 4,089,802; 4,100,103 and 4,251,386 and British Patent specification Nos. 1,156,725; 2,041,319 and 2,048,206. A wide variety of different materials may also be used in making the capsule shells. A popular material for shell formation is the polymerization reaction product between urea and formaldehyde or melamine and formaldehyde, or the polycondensation products of monomeric or low molecular weight polymers of dimethylolurea or methylolated urea with aldehydes. A variety of capsule forming materials are disclosed, for example, in U.S. Pat. Nos. 3,516,846 and 4,087,376 and U.K. Patent Specification Nos. 2,006,709 and 2,062,570.

As shown in these references, the principal utility of microencapsulated materials is in the formation of a surface coated with the microcapsules in a binder. The microcapsules are ruptured by various means to release the material contained therein. In addition to release of physically observable materials such as ink in order to form a visible image, other types of active ingredients such as odor releasing materials, bacteriostatic materials, chemically active materials and the like have been provided in this manner.

U.S Pat. No. 4,186,743 describes the use of microcapsules on a pressure sensitive adhesive between two surfaces on a sanitary napkin. When a cover layer is removed, capsules are broken and the fragrance is released.

U.S. Pat. No. 4,487,801 describes the use of a non-pressure sensitive adhesive layer between two surfaces, the layer having fragrance containing microcapsules therein. Upon separation of the two surfaces, the adhesive and the microcapsules are ruptured, releasing the fragrance. U.S. Pat. No. 4,720,417 shows a similar article in which the two surfaces are coated paper surfaces.

With the wide variety of paper stocks being used in the printing industry, different formulations of adhesive must be made and optimized to obtain the desired bonding and rupture strengths in these fragrance sampling articles.

SUMMARY OF THE INVENTION

A liquid releasing device may be manufactured as follows: Two opposed surfaces are first coated with a first solvent activatable binder layer. A second coating composition comprising a liquid containing microcapsules in a liquid carrying medium is applied between the two coated surfaces and the surfaces are bonded, by the second coating composition or the action of the liquid carrying medium is a solvent, upon drying. The solvent in the coating composition may activate the first binder without dissolving the microcapsules. The mechanical properties of the adhered composite (the rupture force and binding strengths) can be adjusted simply by changing the weight per unit area of the first binder.

DETAILED DESCRIPTION OF THE INVENTION

The present invention relates to an article comprising at least two surfaces, sheets or opposed faces of a folded single sheet temporarily secured by means of a base coating on each of the opposing faces of the sheets and a third adhesive layer having microcapsules dispersed therein. Generally flexible sheets of paper are preferred. Coated paper is preferred and is a conventional and standard item in commerce. It is generally a fibrous sheet having a pigment-bearing resinous coating on one or both surfaces. Usually the pigment provides a white, bone or ivory coloration to the sheet. Most generally pigments producing a white coloration are used. The binder used in the resinous coating is generally colorless and/or transparent. The binder is generally a synthetic or natural organic polymeric material. Typical pigments for producing white coated paper are fine white pigment such as clay, calcium carbonate, titania, silica, zinc oxide, etc. Typical binders include latices (e.g., styrene-butadiene, butadiene-acrylonitrile, etc.), film-forming polymers (e.g., polymethylmethacrylate), and natural resins (e.g., casein, ammonium caseinate, starch, etc.). The coatings usually comprise between 65–90% by weight of pigment, preferably 70–80% by weight of pigment, and 10–35% by weight of binder, preferably 20–30% by weight of binder. Papers having both sides coated are preferred in the advertising trade.

The properties of such paper coatings as are commonly encountered in commerce vary widely from one manufacturer to another and even from lot to lot. This has made it necessary to adjust the composition, coating weight, and coating conditions for each individual production run in order to obtain the best balance of peel force and capsule rupture in the products of the prior art. We have found that a base coating applied to the paper stock prior to the application of the capsule containing layer may greater reduce the variability previously encountered. The base coatings are believed to function, in part, by controlling the rate and degree to which the carrier liquid for the capsule containing layer penetrates the underlying paper. This in turn influences the effective amount and distribution of binder in the dried capsule containing layer and the resulting mechanical properties of the layer. We have further found that it is preferably desirable to select the polymer employed to form the base coat layers from materials which will act as an adhesive for the capsules when wet by the carrier liquid used to apply the capsule containing layer.

In the event that the polymer of the base coat layers is not soluble in or softened by the carrier liquid for capsules, it is desirable to include a separate binder in the capsule containing layer. This binder is usually employed at lower levels than those of the prior art capsule coating systems.

The adhesive material for the capsules must form a bond to the coated surfaces of the sheets which is stronger than the cohesive strength of the adhesive with the capsules dispersed therein. Although it is generally desirable to have an adhesive, the absolute cohesive strength of which is less than its adhesive strength to the coated surface of the coated paper cover sheets, this is not essential. When capsules are included within the adhesive composition, the effective cohesive strength of the adhesive tends to be reduced. Adhesives, which by themselves would cause the sheets to be damaged during separation, can be used in combination with capsules in the practice of the present invention because of lowered effective cohesive strength. The capsules in the present invention may comprise any rupturable capsule containing an active ingredient therein. The active ingredient may be a fragrance, medicinal liquid, one part of a two part reactive system, test indicator, repellent, or the like The tensile rupture strength of the capsules must be such that the cohesive failure of the adhesive results in capsule breakage. It has also been found that the size of the capsules plays a role in the usefulness of capsules within rupturable sheets according to the practice of the present invention. Generally the capsules should have an average diameter between 6 and 500 microns and preferably between 12 and 30 microns when the capsule payload is between 80 and 90% by weight of the total capsule weight. It is highly preferred that the capsules have an average diameter between 14 and 26 microns and it is most preferred that the capsules have a diameter between 15 and 25 microns. These dimensions play a surprisingly important role in the ability to control the percentage of rupture of capsules in the practice of the present invention. With lower payloads (e.g., 70–80%), the capsules should be larger to provide the necessary rupture strength. The broadest range of average capsule size under most conditions would be about 4 to 80 microns. When 8 micron capsules are used, a 90–95% by weight payload is preferred. Eight to thirty micron capsules are generally preferred The capsules should form between 20 and 99 percent by volume of the total adhesive composition, and preferably between 90 and 98 percent of the total composition volume. If certain microcapsule shell materials are used, such as gelatin, the capsule may comprise as much 100% of the adhesive compositions. The absolute peel force tends to be dependent on the weight the base coat and relatively independent of the amount of capsules (up to 50% by weight capsules).

As previously noted, the prior art compositions have to be formulated for differing substrates. This can be a time consuming and expensive effort, particularly for small sampling orders. By practicing the teachings of the present invention, single compositions or pairs of compositions can be used to adhere substantially all polymeric or paper surfaces including uncoated paper stocks. Any commercial base stock may be used.

The essential characteristics and features of the present invention include a process for adhering two surfaces together with a microcapsule filled binder, the process comprising the steps of (a) coating two surfaces with an adhesive which may or may not be a solvent activatable first adhesive, (b) applying a coating composition between said two surfaces, said adhesive composition comprising a liquid carrying medium and microcapsules containing a liquid fill therein (and optionally a second adhesive), (c) and bringing said surfaces into adhesive contact with each other to bind them together The two opposed surfaces may be the same or different. There may be a first adhesive in said base coating composition and a said second adhesive may be present in the capsule composition, said second adhesive also may be the same or different material from said first adhesive. Both adhesives may be swellable, softenable, or soluble the solvent of the adhesive composition. The solvent or carrier liquid also must not quickly dissolve the microcapsules (e.g., in less than one hour). The first adhesive dries to some extent before the capsule coating composition is applied and may be intentionally air dried or oven dried before the adhesive composition is applied.

The solvent may be water or organic solvents or mixtures thereof. The organic solvents may be polar or non-polar, depending upon the solvation requirements of the binders.

The bonding of the surfaces may be effected in a number of alternative fashions. The base coatings on both opposed faces of the sheets may be the sole adhesive coating compositions. This can be done by applying the microcapsule slurry composition between the opposed faces either (1) before complete drying of the base coat so that it can act as an adhesive without further solvent activation (some thermal activation may be desirable), or (2) after drying but with the microcapsule slurry coating composition containing a liquid carrier medium which is an activating solvent for the adhesive in the base coat, or (3) after drying but with the microcapsule slurry coating composition containing sufficient amounts of an adhesive which can bond the two adhesive (polymer) coated opposed faces together. The binder or adhesive should not be a pressure-sensitive adhesive as these perform extremely inefficiently and poorly.

The areas of bonding between the opposed faces can be made discontinuous in a very easy procedural modification. By printing the base coat adhesive composition in a discontinuous manner and not using any significant amount of adhesive (e.g., a polymeric thickener may be used to increase the viscosity of the microcapsule slurry) in the microcapsule slurry coating composition, the opposed faces will be adhered only in those areas where the base coat adhesive has been printed. The slurry carrying medium is usually a solvent for the base coat adhesive in this embodiment. The microcapsules will lightly adhere to the faces of the sheet, but will not rupture upon separation of the opposed faces. This will allow for reuse of the fragrance; i.e., additional microcapsules can be ruptured by scratching after the sheets have been separated.

The binders may be water-soluble, aqueous-swellable, or organic solvent soluble. Preferred binders' are at least water-softenable binders such as polyvinyl pyrrolidone, gelatin, polyvinyl alcohol, hydroxyethyl cellulose, hydroxypropyl cellulose, or may be organic solvent soluble polymers such as polyvinyl ethers, polyacrylates, polyamides, polyester, polyvinyl chloride, polyvinylidene chloride, polylyrene, and mixtures, blends, or copolymers of these types of materials.

It is particularly desirable in the present invention to use an amount of binder in the capsule layer coating composition which is too small to form an adhesive bridge between the two surfaces by itself. This would require the use of binders which are present at less than 10% by weight of the capsule weight, preferably less than 7% and most preferably less than 5% and greater than 0.2%. Larger concentration of binder (e.g., 80%) can be used, but the preferred practice is as just described.

The present invention enables the manufacture of a device for exposing a liquid (e.g., to the atmosphere, said device comprising:

(1) at least two surfaces of coated or uncoated paper bound by an adhesive composition base coat layer, (2) a composition layer between said base or film coat layers on said surfaces containing microcapsules with said liquid within the shell of said microcapsules, and (3) said microcapsules having an average diameter between 4 and 500 micrometers, the cohesive strength of the adhesive composition layer being less than the strength of the bond between said adhesive composition and a coated face of said sheets, the tensile rupture strength of said microcapsules being less than the cohesive strength of the adhesive composition, and the rupture force of said microcapsule containing adhesive composition layer at 50% relative humidity being between at least 2 ounces per linear five-and-one-half inches and less than 45 ounces per linear five-and-one-half inches (greater than 4.0 g/cm and less than 90 g/cm). It is preferred that the rupture strength between the sheets exceeds 8.0 g/cm and is less than 80 g/cm and most preferably exceeds 16 g/cm and is less than 75 g/cm. The minimum strength at this ambient condition (i.e., 23° C. and 50% R.H.) is necessary to keep the sheets from falling apart from forces incurred during handling. This problem has frequently occurred in magazine inserts where coated paper has been used. The maximum limit on the rupture strength is necessary to keep the paper from tearing (termed fiber pull or fiber rupture) before the adhesive and capsules rupture. This would prevent release of the liquid from the capsules.

It is also desirable to have the construction resist the effects of variable ambient conditions. Certain products presently used on uncoated paper stock work in ambient conditions but fail in transit or on storage as the temperature and humidity change. Given the fact that some of these compositions fail at even standard conditions (23° C. and 50% R.H.), they tend to fail worse at more extreme conditions such as 26.5° C. and 80% R.H. or on dry conditions. For example, some binders or capsules are dehydrated by storage in heated warehouses during the winter and become so fragile that simple handling will rupture them. Complaints have been made by purchasers of magazines that all of the various odors in inserts are being released prior to usage of the magazine. The entire magazine tends to have a strong composite odor of many scents rather than being able to provide distinct samples of individual scents. It is therefore desirable that rupture strength exceed 4.0 g/cm after storage at 49° C. and less than 10% R.H. for seventy-two hours. This test may be performed by storage in an oven, removal to a neutral environment (e.g., sealed bag or jar) until the article is at room temperature, and then measuring the rupture strength. It is preferred that the rupture strength is at least 4 to 8.0 g/cm and most preferred that the rupture strength is at least 16 g/cm under those conditions. The article must still display a rupture strength between 4 and 90 g/cm at 23° C. and 50% R.H.

A number of methods have been found which enable these conditions to be met according to the present invention. The use of viscosity increasing agents in the capsule containing coating composition provides a more even coating and one that ruptures before fiber pull begins. The use of additional coatings over the coated paper which contain polymers different from the binder of the adhesive layer and which do not form a solution or chemically bond to the binder of the adhesive layer provides a useful article according to the present invention. The use of larger size capsules tends to weaken the cohesive strength of the adhesive composite and prevent fiber pull. The use of capsules which are not moisture sensitive in combination with these large capsules (i.e., greater than 30 microns and up to 500 microns) provides a useful adhesive layer. Higher capsule-to-binder ratios reduce the cohesive strength of the adhesive, as may the addition of non-viscosity enhancing particulate fillers. The viscosity increasing agents described in U.S. Pat. No. 4,720,417 been found to be useful in the coatings of this invention.

The inorganic particles tend to be preferred. The viscofier enhancers have been found to be necessary in dry weight proportions of the adhesive mix in amounts of from 0.25 to 12% by weight, preferably from 5 to 12% by weight. In general, the weight proportions of materials in the dried adhesive layer according to the present invention are generally as follows:

| Microcapsules | 80%–100% |
|---|---|
| Adhesive | 20%–0% |
| Viscosity Enhancers | 0.0–10% |

The slurry composition may vary from 98% capsules and 2% liquid medium to 10% capsules and 90% liquid medium with 0–50% binder present.

The ability to use coated paper in the manufacture of these articles is important because that material is the standard printing medium of the trade. Those papers enable the highest quality printings to be made in combination with the releasable materials of the present invention.

The nature and composition of the adhesive binder is not critical to the practice of the invention as long as the required functional, adhesive and cohesive properties are met. The adhesive may be pressure sensitive, water or solvent borne or thermally activatable. A single layer of a non-pressure-sensitive adhesive is preferred. There is no need for rejoining the sheets after rupturing of the capsules and so the pressure sensitive function is not necessary.

The base coat layer and the adhesive (with microcapsules) may be applied between two separate sheets in either a continuous or discontinuous patterns. It is usually desirable to leave at least some portion of at least one outer edge of the sheets unbonded so as to provide an area where separation can be easily started. A single sheet may be folded so as to form two facing sheets joined along one edge. The adhesive may be applied on the interior area adjacent to the fold. This provides a folded article that can be readily opened, rupturing the capsules, yet leaves a single artifact rather than two sheets after use.

It is preferred that the capsule-bearing adhesive coated inside portion of the single sheets (e.g., from the fold to the end of the adhesive) constitute from 5 to 40% of the surface area of the sheets. In two sheet constructions, 10 to 95 percent adhesive coverage is used. Some uses may allow for only a single corner to be uncoated so as to provide a starting point for the separation of the sheets, but the 5 to 40% range is preferred with 10 to 30% more preferred in two sheet constructions.

Any class of adhesives including but not limited to polyurethanes, polyacrylates, polyvinyl resins (e.g., polyvinyl alcohol, polyvinyl chloride), polyamides, polyesters, polyolefins, starches, gum arabic, gelatin and the like may be readily used in the practice of the present invention. These materials may be applied from either water or organic solvents depending on the solubility of the individual materials. Washing of the capsules before coating them over the base coat adhesive tends to provide more consistency in their properties by removing low molecular weight, unreacted materials.

In effect, to best practice the present invention it is desirable that certain properties within the article have relative values for each of the materials used. The cohesive strength of the sheet material should exceed the adhesive strength between the base coat binder and the sheet. The adhesive strength of the base coat binder to the sheet should exceed the cohesive strength of the binder. The cohesive strength of the base coat layer and any binder present in the capsule layer should exceed the tensile rupture limits of the capsules.

As previously noted, the size of the capsules has an important effect upon the practice of the present invention. With capsules less than 8 microns, there tends to be less rupturing of the capsules as to prevent the useful and efficient release of materials. Above 50 microns, the particles are so large that additional care is necessary in handling of the sheets and manufacturing procedures. Furthermore, with the large size particles it is extremely difficult to control bursting upon separation of the sheets because of increased effects upon adhesive and cohesive properties of materials in contact with the capsules. The preferred ranges of 8 to 30 and 15 to 25 microns is important to the practice of the present invention. Within these limits, rupture in excess of 50 percent of the capsules can be easily obtained. Rupture in excess of 80 percent of the capsules can often be accomplished in the practice of the present invention within those limits.

The capsules may contain a wide variety of active materials therein. The least useful of materials to be included therein would be coloring agents since separation of the sheets would generally produce uniform coloration rather than a distinct image. The most preferred types of ingredients would be fragrant materials (such as essences and perfumes) or materials which provide chemically active vapors or liquids (e.g., bacteriostats or deodorants) to be wiped on or transferred to another surface. These may or may not also be colored. For example, a testing kit for presence of chemical vapors could be produced by providing material within the capsules which would react with the vapor phase material for which a leak is being investigated. By separating the sheet, rupturing the capsules and exposing the vapor test material, a color forming reaction in the air or on the sheet could be readily observable. Another particularly useful format would be to include the microcapsules within a water-remoistenable adhesive and to use the mixture as the binding adhesive for novelty envelopes. For example, the microcapsules could contain the aromatic essence of baby oil, cake or pizza for invitation envelopes for a baby shower, wedding (or birthday party), or general party, respectively. The sides of the sheets with the capsule-bearing adhesive thereon are preferably printed under the adhesive or adjacent the adhesive.

This invention may be practiced with a number of various modifications that provide new and useful articles and processes. For example, the adhesive composition with capsules may be associated with various printed formats to form novelty items. The exterior sheets or exposed inner face of the sheets may have questions or stories or rhymes, and under the adhesive may be a printed picture answering the question, depicting the story or completing the rhyme, with the released fragrance emphasizing the picture further.

The capsule bearing adhesive layer in the construction of the present invention may also be used for a security device. In an article such as a coupon, lottery ticket or gaming card, the important display could be located under the adhesive. Once the article had been opened and the fragrance released, any subsequent recipient would be aware of its prior use and could be apprised of the possibility of tampering. The adhesive being non-pressure sensitive, it is not repositionable, the sheets are not easily rebonded, and there would be no release of fragrance if the sheets were rebonded with additional non-fragranced adhesive and reopened. The absence or reduced level of fragrance would indicate that the article had been tampered with.

These and other aspects of the present invention will be shown in the following examples.

EXAMPLE I

An oil having the aroma of roses was encapsulated in a urea-formaldehyde resin made according to the process of Example 20 of U.S. Pat. No. 3,516,941. The capsules had an average diameter of about 17 micrometers and an estimated payload of 85% by weight (ratio of oil to total capsule weight).

The following coating formulations were then prepared.

Base Coat
   10% by weight hydroxypropyl cellulose in ethanol

Fragrance Coat
   98% Capsules
   2% hydroxypropyl cellulose

A web off-set printing press with two ovens was used to manufacture the samples. Coated paper stock was printed then dried in the first oven. The base coat was then applied in a stripe over an unprinted area in various amounts and dried in the second oven. The fragrance coat was then applied in various amounts over the dried base coat, the paper folded along the stripe and air dried for twenty-four hours. The data are as follows:

| Sample | Base Coatings Weight (lbs/1300 ft$^2$) | Fragrance Coating (lbs/1300 ft$^2$) |
|---|---|---|
| 1 | 0.500 | 2.50 |
| 2 | 0.625 | 2.50 |
| 3 | 0.625 | 3.00 |
| 4 | 0.625 | 3.50 |

The mechanical strength was greater in samples 2–4 than sample 1 (because of the greater base coat weight) and the fragrance strength was, as expected the greatest in sample 4.

It was found that fragrance delivery is improved by this process since the fracture of the material between the two surfaces occurs primarily in the fragrance coat and not in the base coat.

By making the base coat discontinuous (e.g., leaving the end areas along a fold uncoated) and using the preferred low amounts of binder in the fragrance layer, an area of unruptured capsules will be left on the area uncoated by the base coat layer if the fragrance coat is laid down as a continuous stripe along the fold. This enables an initial release of fragrance upon separation of the surface and a repeat release upon scratching the areas containing intact capsules.

We claim:

1. A method of manufacturing liquid releasing devices comprising the steps of:
   (1) providing two opposed surfaces,
   (2) coating each of said two opposed surfaces with a binder,
   (3) applying a composition between said opposed surfaces with a binder, said composition consisting essentially of microcapsules having a liquid fill therein and a liquid carrying medium free of adhesive, and
   (4) bonding said surfaces together and trapping said microcapsules therebetween with said binder.

2. The method of claim 1 wherein said liquid carrying medium is a solvent for said binder.

3. The method of claim 1 wherein said two opposed surfaces comprise coated paper surfaces.

4. The method of claim 2 wherein said two opposed surfaces comprise coated paper surfaces.

* * * * *